US012570939B2

(12) United States Patent
Lung et al.

(10) Patent No.: US 12,570,939 B2
(45) Date of Patent: Mar. 10, 2026

(54) EXTRACTION APPARATUS AND EXTRACTION METHOD FOR A FERMENTATION MEDIUM

(71) Applicant: MICO-Systems GmbH, Putzbrunn (DE)

(72) Inventors: Gerhard Lung, Stuttgart (DE); Olaf Von Könemann, Putzbrunn (DE); Georg Böhm, Putzbrunn (DE)

(73) Assignee: MICO-Systems GmbH, Putzbrunn (DE)

( * ) Notice: Subject to any disclaimer, the term of this patent is extended or adjusted under 35 U.S.C. 154(b) by 709 days.

(21) Appl. No.: 17/822,376

(22) Filed: Aug. 25, 2022

(65) Prior Publication Data

US 2022/0403311 A1     Dec. 22, 2022

Related U.S. Application Data

(63) Continuation of application No. PCT/EP2021/053984, filed on Feb. 18, 2021.

(30) Foreign Application Priority Data

Feb. 28, 2020     (EP) .................................... 20160130

(51) Int. Cl.
| | |
|---|---|
| *C12M 1/16* | (2006.01) |
| *C12M 1/00* | (2006.01) |
| *C12M 1/04* | (2006.01) |

(52) U.S. Cl.
CPC ............ *C12M 21/16* (2013.01); *C12M 27/04* (2013.01); *C12M 29/26* (2013.01)

(58) Field of Classification Search
None
See application file for complete search history.

(56) References Cited

U.S. PATENT DOCUMENTS

| | | | | | |
|---|---|---|---|---|---|
| 3,251,749 | A | * | 5/1966 | Lipps, Jr. ................ | C12P 19/06 |
| | | | | | 435/910 |
| 5,057,221 | A | * | 10/1991 | Bryant .................. | C02F 3/1231 |
| | | | | | 435/267 |
| 2008/0131960 | A1 | * | 6/2008 | Belongia ................ | C12M 23/26 |
| | | | | | 435/296.1 |

FOREIGN PATENT DOCUMENTS

| | | | |
|---|---|---|---|
| DE | 102007023654 | A1 | 4/2008 |
| DE | 102015220315 | A1 | 4/2017 |
| EP | 1208068 | A1 | 5/2002 |
| EP | 1414938 | B1 | 7/2007 |

(Continued)

OTHER PUBLICATIONS

European Patent Office, International Search Report and Written Opinion in International Patent Application No. PCT/EP2021/053984 (May 20, 2021).

*Primary Examiner* — William H. Beisner

(74) *Attorney, Agent, or Firm* — Leydig, Voit & Mayer, Ltd.

(57) ABSTRACT

An extraction apparatus for a fermentation medium comprises an extraction chamber configured to receive a fermentation medium and comprising a lower portion and an upper portion above the lower portion, as well as a feed device configured to feed at least one gas and one liquid into the lower portion of the extraction chamber, as well as a discharge opening arranged in the upper portion of the extraction chamber and configured to drain a washout liquid, loaded with microorganisms, from the extraction chamber.

17 Claims, 3 Drawing Sheets

(56)        References Cited

FOREIGN PATENT DOCUMENTS

EP        3872053  A1    9/2021
FR        2904308  A1    2/2008

* cited by examiner

Provide a fermentation medium in an extraction chamber    S10

Feed at least one gas and one liquid into a lower portion of the extraction chamber to form a washout liquid, loaded with microorganisms, from the fermentation medium    S12

Drain the washout liquid from an upper portion of the extraction chamber above the lower portion    S14

EXTRACTION APPARATUS AND EXTRACTION METHOD FOR A FERMENTATION MEDIUM

CROSS-REFERENCE TO RELATED APPLICATION

The instant patent application claims priority to International patent application no. PCT/EP2021/053984, filed on Feb. 18, 2021, which International patent application claims priority to European patent application no. EP20160130.9, filed on Feb. 28, 2020, both of which are incorporated herein in their entirety by reference.

TECHNICAL FIELD

The present disclosure relates to an apparatus and a method for extracting a fermentation medium, in particular a fermentation medium containing a compost material, from an extraction chamber, for example to provide a liquid which is loaded with microorganisms and which can be used in agriculture and horticulture as a fertilizer or plant protection agent.

BACKGROUND

In conventional agriculture and horticulture, it is common practice to promote the growing conditions of plants by applying fertilizers and to protect plants against pests by applying herbicides, fungicides and pesticides. From an ecological point of view, many of the chemical substances used for this purpose prove to be questionable. In particular, the large-scale application of such substances can have adverse effects on the ecosystem concerned, especially impairing groundwater quality. The quality and taste of food produced from plants treated in this way can also be negatively affected.

Due to these problems, plant-based fertilizer eluates have already been developed in the past, which are produced by washing out a fermentation medium, for example an organic compost material, and can be applied in liquid form in fields and gardens. Their fertilizing and/or plant-protecting effect is due to the microorganisms which are contained in these eluates and which originate from the fermentation medium.

The European patent specification EP 1 414 938 B1 describes a corresponding method and an apparatus for preparing a liquid loaded with microorganisms, in which a compost material is provided in an enrichment device that is connected to a fermentation tank via lines and pumps. From the fermentation tank, liquid is introduced into the enrichment device from above via a feed line. The liquid washes microorganisms out of the compost material on its way down through the enrichment device and is pumped out of the enrichment device at the bottom and returned to the fermentation tank via a discharge line. In the fermentation tank, further conditioning and processing of the washout liquid loaded with the microorganisms can be carried out under predetermined temperature conditions until the eluate lastly can be removed from the fermentation tank as a fertilizer or plant protection agent.

Apparatuses for controlling the temperature of the fermentation tank and for supplying oxygen to the fermentation tank are also described in the laid-open application (Offenlegungsschrift) DE 10 2007 023 654 A1.

Overview

Against the background of the prior art, there is a need for an apparatus and a method that enable a more efficient washing-out of the fermentation medium and a higher microorganism density in the eluate.

In one aspect, the present disclosure describes an extraction apparatus for a fermentation medium comprises an extraction chamber configured to receive a fermentation medium and comprising a lower portion and an upper portion above the lower portion, as well as a feed device configured to feed at least one gas and one liquid into the lower portion of the extraction chamber, as well as a discharge opening arranged in the upper portion of the extraction chamber and configured to drain a washout liquid, loaded with microorganisms, from the extraction chamber.

The at least one gas and the at least one liquid, which are introduced into the extraction chamber from below, pass through the fermentation medium on their way to the upper discharge opening. In this way, the microorganisms are particularly effectively and completely dissolved from the fermentation medium, so that the washout liquid discharged from the extraction chamber has a particularly high microorganism density, which leads to an increase in the fertilizing and/or plant-protecting effect of the eluate. In particular, feeding the gas together with the liquid from below into the extraction chamber can further promote efficient washing out of the fermentation medium. For example, the gas can help to loosen the fermentation medium and can cause the fed liquid to bubble, so that the fed liquid in the extraction chamber comes into contact with the fermentation medium over a large surface cross-section.

Any organic medium can be used as the fermentation medium within the scope of the present disclosure. In particular, the fermentation medium can be a solid.

In one embodiment, the fermentation medium comprises at least a proportion of a compost material. The compost material can be biologically active and can comprise a large number of living aerobic microorganisms. In particular, green waste material, which can optionally also be enriched with manure, can be used as compost material.

According to some embodiments, additives can also be added to the fermentation medium to promote multiplication of the microorganisms. For example, molasses or vinasse or algae preparations can be used as additives.

Within the scope of the present disclosure, an extraction chamber can be any container or space configured to receive and wash out the fermentation medium. The fermentation medium can be contained in the extraction chamber, for example, loosely or in liquid- and gas-permeable bags.

Within the scope of the present disclosure, the terms "bottom" and "top" or "lower portion" and "upper portion" may denote a relative orientation with respect to a vertical direction of the extraction apparatus. In particular, the lower portion may be closer than the upper portion to a surface on which the extraction apparatus is directly or indirectly supported during operation of the extraction apparatus. The vertical direction may correspond to the direction of a gravitational field so that masses can move along the vertical direction from top to bottom, in particular from the upper portion to the lower portion, under the action of gravity.

The upper portion can be opposite or facing the lower portion in the extraction chamber.

In some embodiments, further (middle) portions of the extraction chamber can be located between the lower portion and the upper portion, spatially separating the upper portion from the lower portion.

A feed device within the scope of the disclosure can be any device that allows the at least one gas and the at least one liquid to be fed into the lower portion of the extraction chamber so that the gas and the liquid come into contact with the fermentation medium received in the extraction chamber and wash out the fermentation medium. The washout can form the washout liquid loaded with microorganisms.

In one embodiment, one gas and one liquid can be fed into the extraction chamber. In other embodiments, multiple gases and/or multiple liquids can be fed into the extraction chamber.

In one embodiment, the gas contains oxygen. In particular, the gas can contain air or can be air.

The fed gas, for example air or oxygen, helps the microorganisms to dissolve effectively from the fermentation medium and to be washed out in high density. In addition, the supply of oxygen promotes the accumulation of aerobic microorganisms in the washout liquid.

In one embodiment, the liquid contains water or is water.

Through a combination of oxygen and water, the fermentation medium can be washed out particularly effectively and a high density of aerobic microorganisms can be achieved in the eluate.

In one embodiment, the feed device can be configured to feed the gas and/or the liquid at a predetermined flow rate into the lower portion of the extraction chamber. For this purpose, in some embodiments, the feed device can comprise valves, in particular throttle valves, and/or pressure regulators to adjust the predetermined flow rate of the gas and/or liquid.

By adjusting the flow rate of the gas and/or the liquid, the washout process and the microorganism density can be purposefully and effectively influenced.

In one embodiment, a flow rate of the gas is at least 10 l/min, in particular at least 15 l/min or at least 18 l/min.

In one embodiment, the flow rate of the gas can be at most 30 l/min, in particular at most 25 l/min or at most 20 l/min.

In one embodiment, a flow rate of the liquid is at least 0.3 l/min, in particular at least 0.5 l/min or at least 0.8 l/min.

In one embodiment, the flow rate of the liquid can be at most 4 l/min, in particular at most 3 l/min or at most 2.5 l/min.

In one embodiment, the feed device can be configured to feed the gas and the liquid separately into the extraction chamber.

In another embodiment, the feed device is configured to feed a mixture of the gas and the liquid into the extraction chamber.

In particular, the feed device can be configured to mix the gas and the liquid, in particular to mix them in a predetermined mixing ratio.

In one embodiment, a mixing ratio of gas to liquid is at least 5 to 1, in particular at least 10 to 1 or at least 15 to 1 or at least 20 to 1.

In one embodiment, the mixing ratio of gas to liquid can be at most 35 to 1, in particular at most 30 to 1 or at most 25 to 1.

The feed device can be configured to feed the gas and/or the liquid into a bottom or a bottom region of the extraction chamber.

In one embodiment, the feed device comprises a membrane which is configured to feed the gas and/or the liquid into the extraction chamber.

By means of a membrane, a mixture of the gas and the liquid can be fed into the extraction chamber in a particularly advantageous way.

The washout of the fermentation medium can also be influenced by a pore size of the membrane. The smaller the pore size, the more finely dispersed is the resulting gas-liquid mixture.

For example, a maximum diameter of pores or openings of the membrane can be considered to be a pore size within the scope of the present disclosure.

In one embodiment, the membrane has a pore width of at most 1 mm, in particular at most 0.8 mm or at most 0.6 mm.

In one embodiment, the membrane has a pore size of at least 0.1 mm, in particular at least 0.3 mm or at least 0.5 mm.

In one embodiment, the extraction apparatus comprises a first screen element and a second screen element, which bound the extraction chamber downwardly and upwardly, respectively, wherein the feed device is configured to feed the gas and/or the liquid through the first screen element into the extraction chamber, and wherein the second screen element is configured and arranged such that the washout liquid leaves the extraction chamber through the second screen element.

In particular, the second screen element can be connected upstream of the discharge opening in the direction of flow.

In some embodiments, the two screen elements form a simple and effective boundary to the extraction chamber within the extraction apparatus. In particular, the first screen element and/or the second screen element can be reversibly removable to allow access to the interior of the extraction chamber and thereby allow easy loading of the extraction chamber with the fermentation medium.

In one embodiment, the first screen element and/or the second screen element has a mesh size of at least 1 mm, in particular of at least 3 mm or at least 5 mm.

In one embodiment, the first screen element and/or the second screen element can have a mesh size of at most 10 mm, in particular at most 8 mm or at most 6 mm.

Within the scope of the present disclosure, a mesh size can be considered to be, for example, a maximum diameter of meshes or openings of the first screen element or the second screen element respectively.

In one embodiment, the first screen element can be arranged above the membrane, in particular downstream of the membrane in the direction of flow.

In this way, the first screen element can protect the membrane from clogging with the fermentation medium. At the same time, the gas-liquid mixture emitted from the membrane can pass through the meshes of the first screen element and wash out the fermentation medium.

Within the scope of the present disclosure, a discharge opening of the extraction apparatus can be understood as any opening that is in the upper portion of the extraction chamber and that is configured and suitable for draining the liquid supplied via the feed device out of the extraction chamber after its contact with the fermentation medium.

The discharge opening can be formed as one continuous opening. In another embodiment the discharge opening can comprise a plurality of partial openings, which may be spatially separated.

According to one embodiment, the extraction apparatus comprises a housing in which the extraction chamber is accommodated.

In particular, a fluid channel, in particular a continuous fluid channel, can be formed between an inner wall of the housing and an outer wall of the extraction chamber for receiving and guiding the washout fluid discharged from the extraction chamber.

The fluid channel can be formed with a drain apparatus to drain the washout fluid from the extraction apparatus, for example to conduct it to a fermentation tank.

In one embodiment, the discharge opening comprises an overflow of the extraction chamber.

According to one embodiment, the extraction apparatus comprises a filter element which is connected upstream of the discharge opening in the direction of flow and/or is arranged downstream of the discharge opening. The filter element can be configured to filter the washout liquid before it is drained through the discharge opening.

In one embodiment, the filter element is arranged between the first screen element and the second screen element. In particular, the filter element can be arranged upstream of the second screen element in the direction of flow.

In one embodiment, the filter element comprises a metal filter, in particular a filter made of a chromium-nickel material.

By adjusting a mesh size of the filter element, the washout process can be influenced in some embodiments. The smaller the mesh size, the fewer and smaller fermentation particles are washed out.

Within the scope of the present disclosure, the mesh size of the filter element may denote a maximum diameter of the meshes or openings of the filter element.

In one embodiment, the filter element can have a mesh size of at least 0.1 mm, in particular at least 0.3 mm or at least 0.5 mm.

According to one embodiment, the filter element can have a mesh size of at most 1 mm, in particular at most 0.8 mm or at most 0.6 mm.

In one embodiment, the extraction apparatus additionally comprises a temperature-control device which is configured to selectively heat and/or cool the extraction chamber and/or the gas and/or the liquid.

In this way, a temperature favorable to the microorganisms can be set in the extraction chamber, or the multiplication of the microorganisms and thus the microorganism density can be influenced.

In one embodiment, the extraction apparatus is configured to be detachably mounted on a fermentation tank, wherein the discharge opening of the extraction apparatus is fluidically couplable to an inlet opening of the fermentation tank.

In this way, the washout liquid discharged from the extraction apparatus can be efficiently and easily transferred to the fermentation tank, where the microorganisms can be multiplied under predetermined temperature conditions.

In a development, the discharge opening of the extraction apparatus can be directly fluidically couplable to the inlet opening of the fermentation tank, in particular fluidically couplable without pipes and hoses.

In some embodiments, the detachable mounting of the extraction apparatus allows, firstly, the extraction apparatus to be detached from the fermentation tank for simplified filling of the extraction chamber.

In addition, washing the fermentation medium out of the extraction apparatus usually takes less time than the subsequent conditioning of the washout liquid in the fermentation tank. In some embodiments, the extraction apparatus can already be removed from the fermentation tank after the washing out and, if necessary, refilled, while the further conditioning of the washout liquid is still taking place in the fermentation tank. In this way, the overall efficiency of the eluate production can be increased.

In addition, a plurality of extraction apparatuses can be fitted successively on the fermentation tank and can also be filled with different fermentation media if necessary, so that the washout liquid from the plurality of extraction apparatuses can be combined and/or mixed in the fermentation tank.

In one embodiment, the discharge opening of the extraction apparatus is located above the inlet of the fermentation tank.

The extraction chamber and the fermentation tank can, in some embodiments, be configured and oriented relative to each other such that the washout liquid can flow from the discharge opening of the extraction apparatus into the fermentation tank under the influence of the force of gravity alone.

In this way, the washout liquid can be transferred from the extraction apparatus into the fermentation tank in a particularly simple and robust manner. Special pipes and pumps for transferring the washout liquid into the fermentation tank can thus be dispensed with in some embodiments, so that the risk of clogging of pipelines and pumps is prevented and the overall reliability of the extraction apparatus can be increased. Therein lies an independent aspect of the present disclosure.

The disclosure therefore also relates to a system comprising an extraction apparatus having any one or all of the features described above and additionally comprising a fermentation tank, wherein the extraction apparatus is configured to be detachably fitted on the fermentation tank and the discharge opening of the extraction apparatus is fluidically couplable to an inlet opening of the fermentation tank.

According to one embodiment, the fermentation tank comprises a temperature-control device which is configured to selectively heat and/or cool the washout liquid.

The conditions for the multiplication of the microorganisms in the fermentation tank can be purposefully adjusted by suitable temperature control of the washout liquid and in this way the microorganism density in the fermentation tank can be increased.

According to one embodiment, the fermentation tank comprises a feed device for feeding a gas into the fermentation tank.

In one embodiment, the gas comprises oxygen. In particular, the gas can contain air or can be air.

The microorganism density of aerobic microorganisms can be increased purposefully by adding oxygen purposefully into the fermentation tank.

A method of extracting a fermentation medium comprises providing a fermentation medium in an extraction chamber, feeding at least one of a gas and a liquid into a lower portion of the extraction chamber to form a washout liquid loaded with microorganisms from the fermentation medium, and draining the washout liquid from an upper portion of the extraction chamber above the lower portion.

According to one embodiment, the gas contains oxygen. In particular, the gas can contain air or can be air.

According to one embodiment, the liquid contains or is water.

In one embodiment, the method comprises selectively adjusting a flow rate of the gas and/or the liquid.

According to one embodiment, a flow rate of the gas is at least 10 l/min, in particular at least 15 l/min or at least 18 l/min.

In one embodiment, a flow rate of the gas can be at most 30 l/min, in particular at most 25 l/min or at most 20 l/min.

According to one embodiment, a flow rate of the liquid is at least 0.3 l/min, in particular at least 0.5 l/min or at least 0.8 l/min.

In one embodiment, a flow rate of the liquid is at most 4 l/min, in particular at most 3 l/min or at most 2.5 l/min.

According to one embodiment, the feeding may comprise conducting a mixture of the gas and the liquid into the extraction chamber.

According to one embodiment, the method comprises mixing the gas and the liquid before feeding them into the extraction chamber, in particular in a predetermined mixing ratio.

In one embodiment, the mixing ratio of gas to liquid can be at least 5 to 1, in particular at least 10 to 1 or at least 15 to 1 or at least 20 to 1.

According to one embodiment, the mixing ratio of gas to liquid is at most 35 to 1, in particular at most 30 to 1 or at most 25 to 1.

In one embodiment, the gas and/or liquid is fed into the extraction chamber via a bottom or bottom region of the extraction chamber.

According to one embodiment, the gas and/or liquid is fed through a membrane into the extraction chamber.

According to one embodiment, the membrane can have a pore width of at most 1 mm, in particular at most 0.8 mm or at most 0.6 mm.

In one embodiment, the membrane can have a pore size of at least 0.1 mm, in particular at least 0.3 mm or at least 0.5 mm.

In one embodiment, the feeding can comprise conducting the gas and/or the liquid through a first screen element into the extraction chamber.

According to one embodiment, the washout liquid can be drained from the extraction chamber through a second screen element.

In one embodiment, the first screen element and/or the second screen element can have a mesh size of at least 1 mm, in particular of at least 3 mm or of at least 5 mm.

According to one embodiment, the first screen element and/or the second screen element has a mesh size of at most 10 mm, in particular at most 8 mm or at most 6 mm.

In one embodiment, the method comprises filtering the washout liquid prior to draining the washout liquid from the extraction chamber, in particular by means of a filter element through which the washout liquid is drained from the extraction chamber.

The filter element can comprise a metal filter, in particular made of a chromium-nickel material.

In one embodiment, the filter element has a mesh size of at least 0.1 mm, in particular at least 0.3 mm or at least 0.5 mm.

In one embodiment, the filter element can have a mesh size of at most 1 mm, in particular of at most 0.8 mm or of at most 0.6 mm.

According to one embodiment, the method comprises controlling the temperature of the extraction chamber and/or the gas and/or the liquid, in particular selectively heating and/or selectively cooling the extraction chamber and/or the gas and/or the liquid.

According to one embodiment, the washout liquid is drained into a fermentation tank, in particular into a fermentation tank arranged below the extraction chamber.

Within the scope of the present disclosure, a fermentation tank can be understood as any container which is configured to receive the washout liquid drained from the extraction apparatus and, if necessary, to further condition it.

According to one embodiment, the washout liquid can be discharged into the fermentation tank under the action of the force of gravity alone.

In one embodiment, the method comprises detachably fitting the extraction chamber on the fermentation tank.

According to one embodiment, the method comprises controlling the temperature of the washout liquid and/or the fermentation tank, in particular selectively heating and/or selectively cooling the washout liquid and/or the fermentation tank.

According to one embodiment, the method comprises feeding a gas into the fermentation tank.

In one embodiment, the gas contains oxygen. In particular, the gas can contain or can be air.

BRIEF DESCRIPTION OF THE DRAWINGS

The features and numerous advantages of the extraction apparatus and/or of the extraction method according to the present disclosure can best be understood from a detailed description of embodiments with reference to the accompanying drawings, in which.

DESCRIPTION OF EMBODIMENTS

Figure 1:
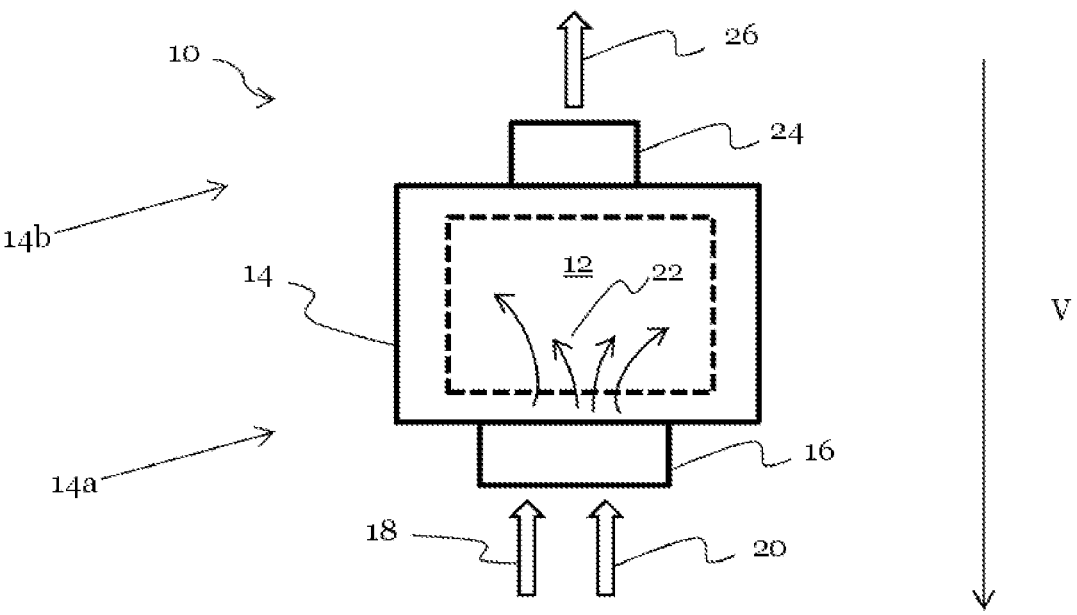
FIG. 1 shows a schematic illustration of an extraction apparatus according to one embodiment.

FIG. 1 is a schematic illustration of an extraction apparatus 10, as can be used, for example, for washing out a fermentation medium 12 in order to provide a washout liquid loaded with microorganisms, which—if necessary after further conditioning and processing—can be used, for example, as an organic fertilizer or organic plant protection agent.

The fermentation medium can in particular be formed at least partially from a compost material. For example, green waste material, which can optionally also be enriched with manure, has proven to be suitable as compost material. Particularly high extraction results can also be achieved with bark compost material, which is additionally distinguished by a high regenerative capacity.

The washout liquid can include useful aerobic microorganisms from the group of antagonists, which are effective, for example, against parasitic fungal diseases. It is suitable, among other things, for the treatment of lawn substrates as well as for the growth promotion of crops in the field of agriculture, especially in the field of vegetable cultivation. Other possible applications include vine and hop cultivation, pond care, disinfection, but also the reduction of odor emissions and the volume of landfills. However, these are only illustrative examples. The extraction apparatus 10 can be advantageously used in a variety of extraction processes.

For further details of possible fermentation media, including any additives that may be used, reference is made to European application EP 1 414 938 B1 and to the laid-open application (Offenlegungsschrift) DE 10 2007 023 654 A1.

The extraction apparatus 10 shown in FIG. 1 comprises an extraction chamber 14 configured to receive inside it the fermentation medium 12, for example the compost material, loose or packed in a gas- and liquid-permeable bag or container.

As further shown in FIG. 1, the extraction apparatus 10 also comprises a feed device 16 arranged in a lower portion 14a of the extraction chamber 14 and configured to feed at least one gas stream 18, for example oxygen or air, and at least one liquid stream 20, for example water, into the lower portion 14a of the extraction chamber 14. The feed device 16 can additionally comprise, in some embodiments, throttle valves (not shown in FIG. 1) which make it possible to selectively and independently adjust a pressure and/or a flow rate of the gas stream 18 and a pressure and/or a flow rate of the liquid stream 20.

In some embodiments the feed device 16 can feed the gas stream 18 and the liquid stream 20 into the extraction chamber 14 as two spatially separated streams. In other embodiments the feed device 16 is configured to mix the gas stream 18 and the liquid stream 20, for example to mix them in a predetermined mixing ratio, and to feed the resulting gas-liquid mixture 22 into the extraction chamber 14.

For example, the feed device 16 can be configured to adjust the flow rate of the gas stream 18 in a range between 18 l/min and 20 l/min and to adjust the flow rate of the liquid stream 20 in a range between 0.85 l/min and 2.4 l/min.

The gas-liquid mixture 22 rises in the extraction chamber 14 from the lower portion 14a upwardly towards an upper portion 14b of the extraction chamber 14, which is opposite the lower portion 14a, and passes through the fermentation medium 12 on its way, so that the gas-liquid mixture 22 washes out the fermentation medium 12 to form a washout liquid loaded with microorganisms.

Since the gas-liquid mixture 22 enters the extraction chamber 14 from below and permeates and mixes through the fermentation medium 12 received therein, a particularly effective and efficient washing out occurs. The gas content in the gas-liquid mixture 22 leads to a loosening and an increase in the surface area of the fermentation medium 12, whereby the liquid can act on the fermentation medium 12 particularly effectively and along an increased surface area, so that the effectiveness of the washing out is additionally increased.

In the upper portion 14b, the extraction chamber 14 comprises a discharge opening 24, which is configured to drain the washout liquid loaded with microorganisms from the extraction chamber 14, for example as a washout liquid stream 26 to a fermentation tank (not shown in FIG. 1).

In FIG. 1 (and also in the embodiments described below with reference to FIGS. 2 and 3), the relative terms "bottom" and "top" indicate an orientation with respect to a vertical direction V of the extraction apparatus 10 in operation, wherein the lower portion 14a is closer than the upper portion 14b to a surface on which the extraction apparatus 10 is directly or indirectly supported in operation. The vertical direction V also corresponds to the direction of a gravitational acceleration acting on the extraction apparatus 10 during operation of the extraction apparatus 10.

The gas-liquid mixture 22 thus rises up from the lower portion 14a, against the vertical direction V indicating the force of gravity, through the extraction chamber 14 and the fermentation medium 12 received therein, effectively washing out the fermentation medium 12 and exiting the extraction chamber 14 as a washout liquid stream 26 via the discharge opening 24 formed in the upper portion 14b of the extraction chamber 14.

Figure 2:
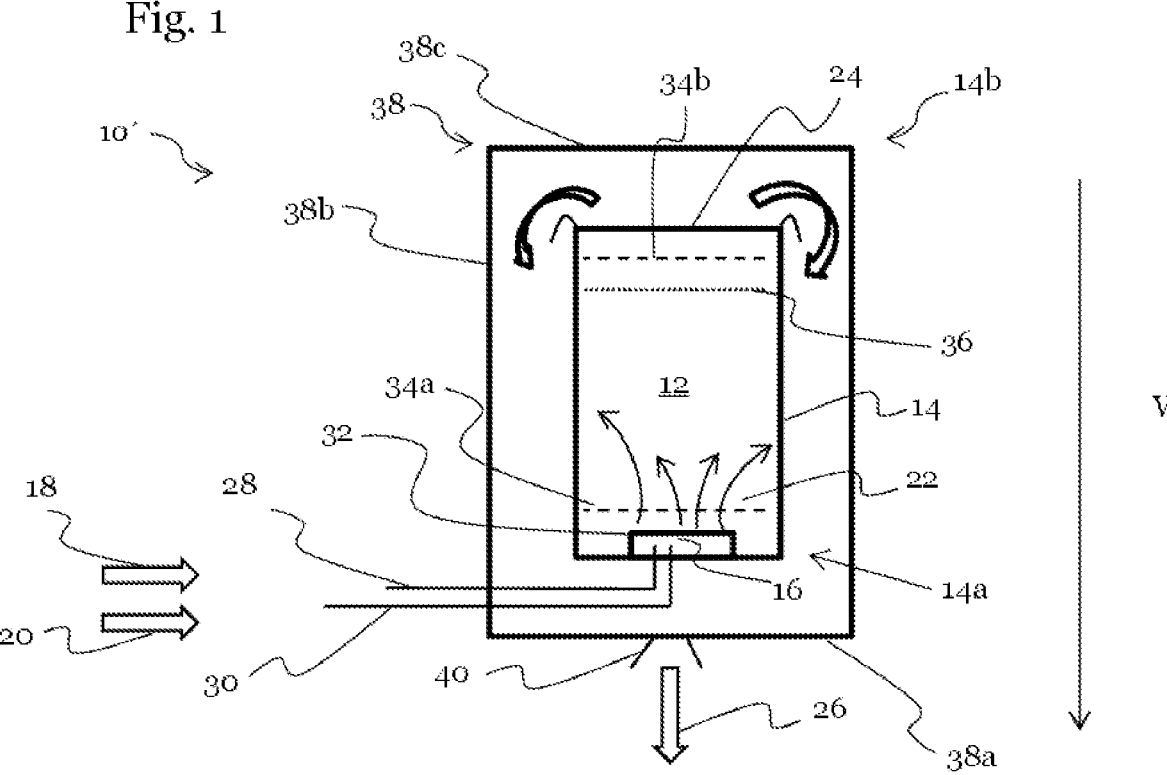
FIG. 2 shows a schematic cross-sectional illustration of an extraction apparatus according to one embodiment.

FIG. 2 shows an embodiment of an extraction apparatus 10' in a schematic cross-sectional view. The extraction apparatus 10' is largely similar to the extraction apparatus 10 described above with reference to FIG. 1, and corresponding components are marked with the same reference signs. In the following, the extraction apparatus 10' will therefore only be described in detail insofar as it differs from the extraction apparatus 10.

The extraction apparatus 10' comprises a hollow-cylindrical housing 38 having a circular bottom wall 38a at its underside, side walls 38b along its periphery, and a circular lid wall 38c at its top side. Inside the housing 38, the extraction chamber 14 is received as an upwardly open hollow cylinder and can therefore be quickly and easily charged with the fermentation medium 14 from above through the discharge opening 24 after removing the lid wall 38c of the housing 38. Between the bottom wall 38a of the housing 38 and the underside of the extraction chamber 14, as well as between the side walls 38b of the housing 38 and the side walls of the extraction chamber 14, a continuous hollow space is formed which can serve as a flow channel for the washout liquid exiting from the discharge opening 24.

The gas stream 18 is supplied to the feed device 16 in the lower portion 14a of the extraction chamber 14 via a gas supply line 28, which is passed through the side wall 38b of the housing 38 in a fluid-tight manner and is connected, for example, to an air compressor or an oxygen source (not shown), and the liquid stream 20 is supplied via a liquid supply line 30, which is also passed through the side wall 38b of the housing 38 in a fluid-tight manner and is connected, for example, to a fresh water connection (not shown). Both the gas supply line 28 and the liquid supply line 30 can be formed with throttle valves or shut-off valves (not shown), for example solenoid valves, which allow the gas stream 18 or the liquid stream 20 to be set to predetermined flow rates.

The feed device 16 is arranged in the bottom region of the extraction chamber 14 and mixes the gas stream 18 and the liquid stream 20 in a predetermined mixing ratio, for example in the ratio 15:1 or 20:1, and discharges the resulting gas-liquid mixture 22 into the interior of the extraction chamber 14 via a membrane 32 provided with pores, for example a plastics membrane. The pores of the membrane 32 may, for example, have a diameter of 0.5 mm or less.

As can additionally be seen in the cross-sectional view of FIG. 2, the extraction apparatus 10' in the embodiment shown has a first (lower) screen element 34a and a second (upper) screen element 34b in the extraction chamber 14, which bound a receiving space for the fermentation medium 12 downwardly and upwardly. The screen elements 34a and 34b can, for example, have meshes with a diameter of 3 mm. The first screen element 34a prevents the fermentation medium 12 from resting directly on the membrane 32 of the feed device 16 and clogging it. The second screen element 34b prevents the fermentation medium 12 from being flushed out through the discharge opening 24 during operation. The second screen element 34b can in particular be designed to be detachable and removed from the extraction chamber 14 in order to facilitate filling of the extraction chamber 14 with the fermentation medium 12 from above through the discharge opening 24.

The cross-sectional view of FIG. 2 also shows a filter element 36, which is arranged in the upper portion 14b of the extraction chamber 14 immediately below the second screen element 34b and is designed to filter suspended particles from the washout liquid. The filter element 36 can, for example, be made of a chromium-nickel material with a thickness of 0.8 mm and a mesh size of 0.5 mm×0.5 mm.

The gas-liquid mixture 22 exiting the membrane 32 flows through the first screen element 34a and washes out the fermentation medium 12 received in the extraction chamber 14 so as to form a washout liquid loaded with microorganisms, as described above with reference to FIG. 1. The washout liquid is filtered through the filter element 36 and passes through the meshes of the second screen element 34b to the discharge opening 24, which in the embodiment of FIG. 2 is formed as an overflow, as indicated schematically by the two arrows indicating an overflow of the washout liquid over the edge of the extraction chamber 14.

The washout liquid exiting the extraction chamber 14 flows downwardly along the vertical direction V in the fluid channel formed between the outer wall of the extraction chamber 14 and the inner wall of the housing 38 and collects above the bottom wall 38a of the extraction apparatus 10', from where it can exit the extraction apparatus 10' as a washout liquid stream 26 through a closable outlet valve 40. The washout liquid stream 26 discharged from the extraction apparatus 10' can, for example, be fed to a fermentation tank, as described in further detail below with reference to FIG. 3.

Figure 3:
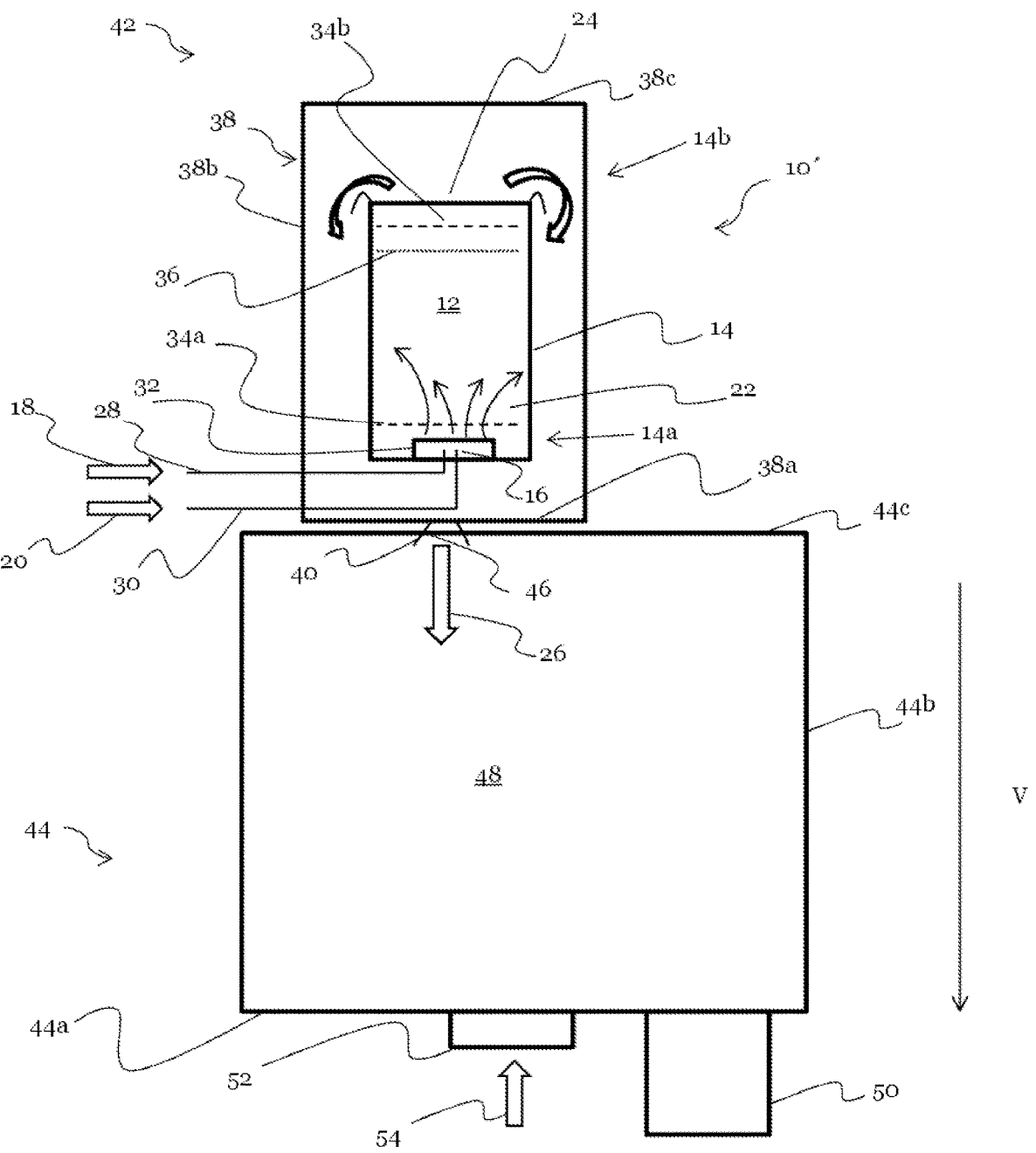
FIG. 3 shows a schematic cross-sectional view of an extraction apparatus interacting with a fermentation tank according to one embodiment.

FIG. 3 shows a schematic cross-sectional view of an extraction system 42 according to an embodiment comprising the extraction apparatus 10' as described above with reference to FIGS. 1 and 2, and a fermentation tank 44.

In the embodiment shown, the fermentation tank 44 is formed as a cylindrical and closed hollow container for holding a volume of washout liquid 48 and comprises a circular bottom wall 44a at its underside, side walls 44b along its periphery and a circular lid wall 44c at its top side. Its volume can be 1000 l, for example.

In the illustration of FIG. 3, the extraction apparatus 10' is detachably seated with its bottom wall 38a on a top side of the fermentation tank 44, for example on its lid wall 44c, so that the extraction chamber 14 and in particular its discharge opening 24 lie above the fermentation tank 44 in the vertical direction V. The extraction apparatus 10' is detachably couplable to the fermentation tank 44 such that the outlet valve 40 in the bottom wall 38a of the extraction apparatus 10' is fluidically connected to an inlet opening 46 in the lid wall 44c of the fermentation tank 44.

In operation, therefore, with the outlet valve 40 of the extraction apparatus 10' open and the inlet opening 46 of the fermentation tank 44 open, the washout liquid exiting from the extraction chamber 14 can flow from the extraction chamber 14 into the fermentation tank 44 solely under the influence of the force of gravity as a washout liquid stream 26, without the need for pumps or compressors. Since the extraction apparatus 10' sits with its bottom wall 38a directly on the lid wall 44c of the fermentation tank 44, external connecting lines or connecting hoses between the extraction apparatus 10' and the fermentation tank 44 can also be largely dispensed with, so that the extraction system 43 as a whole is particularly robust and insensitive to maintenance.

In typical applications of the extraction system 42, the washing out occurs over a shorter period of time, for example 7 hours to 20 hours, than the residence time of the washout liquid in the fermentation tank, which can be up to 60 hours.

For example, a fermentation tank 44 with a capacity of 1000 l can be filled in approximately 20 hours at a flow rate of the liquid stream 20 of 0.85 l/min, and in approximately 7 hours at a flow rate of the liquid stream 20 of 2.4 l/min. The gas stream 18 can have a flow rate in the range of 18-20 l/min in each case.

The extraction system 42 offers the advantage that the extraction apparatus 10' can be separated from the fermentation tank 44, cleaned and refilled after the washing out has taken place, while the washout liquid 48 in the fermentation tank 44 is further conditioned, for example suitably temperature-controlled or provided with additives, to produce an eluate. If necessary, another extraction apparatus, possibly with a different fermentation medium, can also be fitted to the fermentation tank 44 and washed out in the meantime. The overall efficiency of the eluate production can be increased in this way.

In some embodiments, the washout liquid 48 received in the fermentation tank 44 can be temperature-controlled, for example selectively heated or cooled, by a temperature-control device 50 to set the washout liquid 48 to a predetermined temperature suitable for multiplication of the microorganisms. For example, the temperature-control device 50 can be controlled in such a way that the temperature of the washout liquid is maintained in the range of 20-25° C.

Via a gas feed device 52 of the fermentation tank 44, which can be arranged, for example, in the bottom wall 44a of the fermentation tank 44, a gas stream 54, for example air from a compressor (not shown) or oxygen from a gas tank (not shown), can be selectively fed to the washout liquid 48 in the fermentation tank 44 in order to additionally promote the multiplication of the microorganisms in the fermentation tank 44 and thus the production of an eluate which is effective for fertilization or plant protection.

For further details and possibilities of the embodiment of the extraction apparatus and the fermentation tank, we refer to the European patent specification EP 1 414 938 B1 as well as the laid-open application (Offenlegungsschrift) DE 10 2007 023 654 A1.

Figure 4:
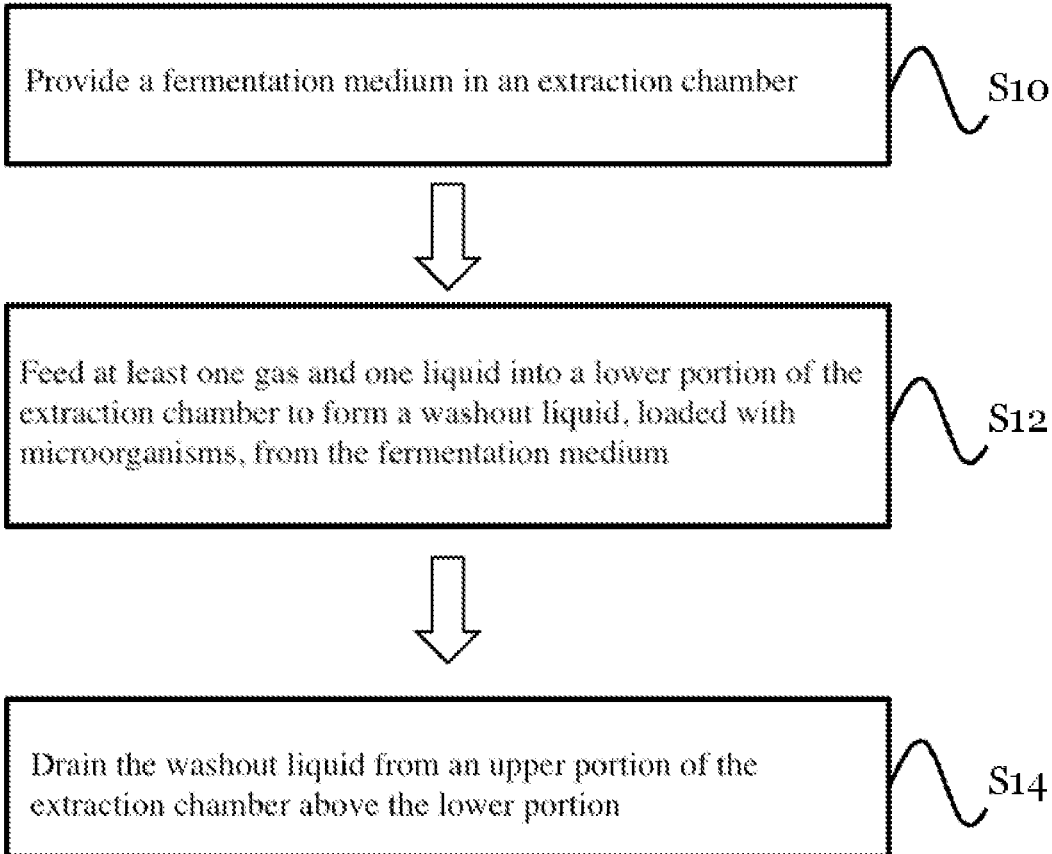
FIG. 4 shows a flow diagram of an extraction method according to one embodiment.

FIG. 4 shows a flow diagram of a method for extracting a fermentation medium according to one embodiment.

In a first step S10, the method comprises providing a fermentation medium in an extraction chamber, for example in an extraction chamber as described above with reference to the embodiments of FIGS. 1 to 3.

In a subsequent second step S12, the method comprises feeding at least one gas and at least one liquid into a lower portion of the extraction chamber to form a washout liquid, loaded with microorganisms, from the fermentation medium.

In a subsequent third step S14, the method comprises draining the washout liquid from an upper portion of the extraction chamber above the lower portion.

The description of these embodiments and figures serve only to explain the extraction apparatus or extraction method of the present disclosure, and is not intended, however, to limit them. The scope of protection results from the appended claims.

| List of reference signs | |
| --- | --- |
| 10, 10' | extraction apparatus |
| 12 | fermentation medium, compost material |
| 14 | extraction chamber |
| 14a | lower portion of the extraction chamber 14 |
| 14b | upper portion of the extraction chamber 14 |
| 16 | feed device |
| 18 | gas stream |
| 20 | liquid stream |
| 22 | gas-liquid mixture |
| 24 | discharge opening |
| 26 | washout liquid stream |
| 28 | gas supply line |
| 30 | liquid supply line |
| 32 | membrane |
| 34a | first/lower screen element |
| 34b | second/upper screen element |
| 36 | filter element |
| 38 | housing of the extraction apparatus 10' |
| 38a | bottom wall of the extraction apparatus 10' |
| 38b | side walls of the extraction apparatus 10' |
| 38c | lid wall of the extraction apparatus 10' |

-continued

List of reference signs

| | |
|---|---|
| 40 | outlet valve of the extraction apparatus 10' |
| 42 | extraction system |
| 44 | fermentation tank |
| 44a | bottom wall of the fermentation tank 44 |
| 44b | side walls of the fermentation tank 44 |
| 44c | lid wall of the fermentation tank 44 |
| 46 | inlet opening of the fermentation tank 44 |
| 48 | washout liquid |
| 50 | temperature-control device of the fermentation tank 44 |
| 52 | gas feed device of the fermentation tank 44 |
| 54 | gas stream |

What is claimed is:

1. An extraction apparatus for a fermentation medium, comprising:

an extraction chamber configured to receive a fermentation medium and comprising a lower portion and an upper portion above the lower portion;

a feed device configured to feed at least one gas and at least one liquid into the lower portion of the extraction chamber;

a discharge opening arranged in the upper portion of the extraction chamber and configured to drain a washout liquid, the washout liquid being loaded with microorganisms, from the extraction chamber; and a fermentation tank having an inlet opening, wherein the extraction chamber is detachably seated on the fermentation tank, and wherein the discharge opening is fluidically couplable to the inlet opening of the fermentation tank.

2. The extraction apparatus according to claim 1, wherein the at least one gas contains oxygen.

3. The extraction apparatus according to claim 2, wherein the at least one gas contains air or is air.

4. The extraction apparatus according to claim 1, wherein the at least one liquid contains water or is water.

5. The extraction apparatus according to claim 1, wherein the feed device is configured to feed the at least one gas and/or the at least one liquid at a predetermined flow rate into the lower portion of the extraction chamber.

6. The extraction apparatus according to claim 1, wherein the feed device is configured to mix the at least one gas and the at least one liquid.

7. The extraction apparatus according to claim 6, wherein the feed device is configured to mix the at least one gas and the at least one liquid in a predetermined mixing ratio.

8. The extraction apparatus according to claim 1, wherein the feed device comprises a membrane configured to feed the at least one gas and/or the at least one liquid into the extraction chamber.

9. The extraction apparatus according to claim 1, further comprising:

a first screen element and a second screen element, the first and second screen elements disposed to bound the extraction chamber downwardly and upwardly;

wherein the feed device is configured to feed the at least one gas and the at least one liquid through the first screen element into the extraction chamber; and wherein the second screen element is configured and arranged such that the washout liquid leaves the extraction chamber through the second screen element.

10. The extraction apparatus according to claim 9, wherein the feed device comprises a membrane configured to feed the at least one gas and/or the at least one liquid into the extraction chamber, and wherein the first screen element is arranged above the membrane.

11. The extraction apparatus according to claim 1, further comprising:

a filter element disposed upstream of the discharge opening in a direction of flow, wherein the filter element is configured to filter the washout liquid before the washout liquid is drained through the discharge opening.

12. An extraction apparatus for a fermentation medium, comprising:

an extraction chamber configured to receive a fermentation medium and comprising a lower portion and an upper portion above the lower portion;

a feed device configured to feed at least one gas and at least one liquid into the lower portion of the extraction chamber;

a discharge opening arranged in the upper portion of the extraction chamber and configured to drain a washout liquid, the washout liquid being loaded with microorganisms, from the extraction chamber;

a first screen element and a second screen element, the first and second screen elements disposed to bound the extraction chamber downwardly and upwardly, wherein the feed device is configured to feed the at least one gas and the at least one liquid through the first screen element into the extraction chamber, and wherein the second screen element is configured and arranged such that the washout liquid leaves the extraction chamber through the second screen element; and a filter element disposed upstream of the discharge opening in a direction of flow, wherein the filter element is configured to filter the washout liquid before the washout liquid is drained through the discharge opening, wherein the filter element is arranged between the first screen element and the second screen element.

13. The extraction apparatus according to claim 12, further comprising:

a fermentation tank having an inlet opening;

wherein the extraction chamber is detachably seated on the fermentation tank; and wherein the discharge opening is fluidically couplable to the inlet opening of the fermentation tank.

14. A method for extracting a fermentation medium, comprising:

providing a fermentation medium in an extraction chamber;

feeding at least one gas and at least one liquid into a lower portion of the extraction chamber, using a feed device, to form a washout liquid, the washout liquid being loaded with microorganisms, from the fermentation medium; and draining the washout liquid from an upper portion of the extraction chamber, the upper portion being disposed above the lower portion, wherein the washout liquid is drained into a fermentation tank.

15. The method according to claim 14, further comprising selectively adjusting a flow rate of the at least one gas and/or a flow rate of the at least one liquid using the feed device.

16. The method according to claim 14, wherein the fermentation tank is disposed below the extraction chamber.

17. The method according to claim 14, further comprising detachably fitting the extraction chamber on the fermentation tank.

* * * * *